(12) United States Patent
Koltz et al.

(10) Patent No.: US 12,064,357 B2
(45) Date of Patent: Aug. 20, 2024

(54) SYSTEM AND METHOD OF BONE PROCESSING

(71) Applicant: MEDTRONIC XOMED, INC., Jacksonville, FL (US)

(72) Inventors: Michael L. Koltz, Jacksonville, FL (US); Louis M. Shadeck, Jacksonville, FL (US); David John Little, II, Ponte Vedra, FL (US); Gerould Winthrop Norman, Jacksonville, FL (US); Dana A. Oliver, Jacksonville, FL (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 655 days.

(21) Appl. No.: 17/180,199

(22) Filed: Feb. 19, 2021

(65) Prior Publication Data
US 2021/0169663 A1    Jun. 10, 2021

Related U.S. Application Data

(60) Division of application No. 16/721,041, filed on Dec. 19, 2019, now Pat. No. 11,219,537, which is a
(Continued)

(51) Int. Cl.
*A61F 2/46* (2006.01)
*A22C 17/04* (2006.01)
(Continued)

(52) U.S. Cl.
CPC ............ *A61F 2/4644* (2013.01); *A22C 17/04* (2013.01); *A22C 17/06* (2013.01);
(Continued)

(58) Field of Classification Search
CPC ................... A22C 17/06; A61F 2/4644; A61F 2002/4645; B27L 11/02
See application file for complete search history.

(56) References Cited

U.S. PATENT DOCUMENTS

| | | | |
|---|---|---|---|
| 1,758,702 A | 5/1930 | Jacobson | |
| 2,682,376 A | 6/1954 | Frank | |

(Continued)

FOREIGN PATENT DOCUMENTS

| | | |
|---|---|---|
| CA | 711844 | 6/1965 |
| CN | 2358841 | 1/2000 |

(Continued)

OTHER PUBLICATIONS

Dr. Andres Stricker, "Innovative Bone Mill Concept Simplifies Augmentation", B Braun Sharing Expertise, 3 pages.
(Continued)

*Primary Examiner* — Andrew Yang
(74) *Attorney, Agent, or Firm* — Carter, DeLuca & Farrell LLP

(57) ABSTRACT

A system and method of processing bone is disclosed. A tissue separator is utilized to separate tissue comprising at least one of muscle, periosteum and connective tissue from bone in a safe, sterile and efficient manner. In one aspect, the particle reducer can include an impeller positioned with respect to a cutting surface on a drum. At least one of the impeller and the drum is rotated by a power source such that harvested tissue frictionally engages the cutting surface. In another aspect, a source of pressurized fluid can be directed at tissue to separate bone from non-bone tissue.

16 Claims, 13 Drawing Sheets

Related U.S. Application Data division of application No. 14/287,733, filed on May 27, 2014, now abandoned, which is a continuation of application No. 12/683,707, filed on Jan. 7, 2010, now Pat. No. 8,740,114.

(51) Int. Cl.
*A22C 17/06* (2006.01)
*B02C 19/00* (2006.01)
*B02C 19/11* (2006.01)

(52) U.S. Cl.
CPC .......... *B02C 19/0056* (2013.01); *B02C 19/11* (2013.01); *A61F 2002/4645* (2013.01); *A61F 2002/4646* (2013.01)

(56) References Cited

U.S. PATENT DOCUMENTS

| | | | |
|---|---|---|---|
| 2,938,558 | A | 5/1960 | Urschel |
| 3,248,752 | A | 5/1966 | Segur et al. |
| 3,559,706 | A | 2/1971 | Conrad et al. |
| 3,656,528 | A | 4/1972 | Mencacci |
| 3,722,032 | A | 3/1973 | Draper et al. |
| 3,799,457 | A | 3/1974 | Ward et al. |
| 3,896,522 | A | 7/1975 | Lapeyre et al. |
| 3,958,763 | A | 5/1976 | Paoli |
| 3,979,196 | A | 9/1976 | Frank et al. |
| 3,989,196 | A | 11/1976 | Urschel |
| 3,989,198 | A | 11/1976 | Blasko |
| 4,042,176 | A | 8/1977 | Beck et al. |
| 4,186,216 | A | 1/1980 | Roth |
| 4,638,954 | A | 1/1987 | Poss |
| RE32,531 | E | 10/1987 | Beck et al. |
| 4,796,818 | A | 1/1989 | Thoma |
| 5,041,055 | A | 8/1991 | Roth |
| 5,087,420 | A | 2/1992 | Jackson |
| 5,340,036 | A | 8/1994 | Riley |
| 5,437,572 | A | 8/1995 | Billington, III |
| 5,797,871 | A | 8/1998 | Wolfinbarger, Jr. |
| 6,024,735 | A | 2/2000 | Wolfinbarger, Jr. |
| 6,045,070 | A | 4/2000 | Davenport |
| 6,060,102 | A | 5/2000 | Erasmus et al. |
| 6,318,651 | B1 | 11/2001 | Spiering |
| 6,402,070 | B1 | 6/2002 | Ishida et al. |
| 6,464,156 | B1 | 10/2002 | Wexell |
| 6,685,428 | B1 | 2/2004 | Freudenberg |
| 6,755,365 | B1 | 6/2004 | Meredith |
| 6,824,087 | B2 | 11/2004 | McPherson et al. |
| 7,131,605 | B2 | 11/2006 | McPherson et al. |
| 7,232,439 | B2 | 6/2007 | Ciarrocca |
| 8,740,114 | B2 | 6/2014 | Koltz et al. |
| 2003/0014124 | A1 | 1/2003 | Wolfinbarger, Jr. et al. |
| 2003/0055316 | A1 | 3/2003 | Brannon |
| 2003/0065399 | A1 | 4/2003 | Brannon |
| 2004/0000605 | A1 | 1/2004 | McPherson et al. |
| 2004/0059282 | A1 | 3/2004 | Flock et al. |
| 2004/0059364 | A1 | 3/2004 | Gaskins et al. |
| 2005/0070892 | A1 | 3/2005 | Ciarrocca |
| 2005/0234464 | A1 | 10/2005 | Brannon |
| 2006/0226267 | A1 | 10/2006 | McPherson et al. |
| 2007/0149881 | A1 | 6/2007 | Rabin |
| 2008/0161649 | A1 | 7/2008 | Deshmukh |
| 2010/0092563 | A1 | 4/2010 | Raffaele et al. |
| 2010/0130666 | A1 | 5/2010 | Hart et al. |
| 2011/0236547 | A1 | 9/2011 | Hultin et al. |
| 2014/0263778 | A1 | 9/2014 | Koltz et al. |
| 2020/0121475 | A1 | 4/2020 | Koltz et al. |

FOREIGN PATENT DOCUMENTS

| | | |
|---|---|---|
| CN | 101252849 | 8/2008 |
| CN | 101287417 | 10/2008 |
| CN | 201360507 | 12/2009 |
| EP | 0973402 | 12/2002 |
| EP | 1629754 | 3/2006 |
| EP | 2599455 | 6/2013 |
| WO | 2005/115625 | 12/2005 |

OTHER PUBLICATIONS

PCT Search Report, PCT/US2010/061988, Date of mailing Mar. 1, 2011, 6 pages.
Biomet, Inc., "The Mill, Bone Mill System," Form No. Y-BMT-527/093097, pp. 2 (1997). <http://www.biomet.com>.
Citagenix Inc., "Osteodisc," GP-5065.0, pp. 1 (Nov. 2005). <www.citagenix.com>.

SYSTEM AND METHOD OF BONE PROCESSING

CROSS-REFERENCE TO RELATED APPLICATIONS

This application is a divisional of U.S. patent application Ser. No. 16/721,041, filed Dec. 19, 2019, which is a divisional of U.S. patent application Ser. No. 14/287,733, filed May 27, 2014, entitled "System and Method of Bone Processing," now abandoned, which is a continuation of U.S. patent application Ser. No. 12/683,707, filed Jan. 7, 2010, entitled "System and Method of Bone Processing" now U.S. Pat. No. 8,740,114, the entire teachings of which are incorporated herein by reference.

BACKGROUND

Morselized bone particles are used in various medical and surgical procedures. For example, finely morselized bone particles can be used for spinal fusion, to repair defects caused by trauma, transplant surgery, or tissue banking. In order to process bone for use in a medical or surgical procedure, several bone processing steps are taken. In one example procedure, a tissue sample including bone is surgically removed (i.e., harvested) from a patient. After removal of the bone from the patient, non-bone tissue (e.g., muscle, periosteum, connective tissue) is removed from the bone in order to prepare the bone for morselizing. Current bone processing approaches to remove the non-bone tissue can be time consuming, labor intensive and hazardous to healthcare personnel (e.g., cutting through gloves). In one example, a technician uses a scalpel to remove non-bone tissue from bone by hand. Hand removal of the non-bone tissue using a scalpel lasts approximately 45 minutes and is prone to operator fatigue and possible injury. Once non-bone tissue is removed from the bone, denuded bone can further be processed by a bone mill to produce morselized bone particles. In any event, it is important for bone processing in a medical environment to be performed in a sterile manner. Additionally, it is important for bone processing steps to be performed efficiently and in a safe, reliable manner.

SUMMARY

Concepts presented herein relate to aspects of bone processing. In one aspect, a method includes positioning bone at least partially covered in non-bone tissue comprising at least one of muscle, periosteum and connective tissue in a bone denuding device. A power source of the bone denuding device is operated to separate the tissue from the bone to produce denuded bone. A bone milling device is operated to morselize the denuded bone and produce morselized bone particles.

In another aspect, a denuder includes a cutting drum having a cutting surface and an impeller positioned within the cutting drum. A shaft is coupled to at least one of the impeller and the drum to rotate therewith and a power source is coupled to the shaft to provide rotational force thereto.

In yet another aspect, a tissue separator is coupleable to a power source for use in removing non-bone tissue comprising at least one of muscle, periosteum and connective tissue from a bone. The tissue separator includes an external casing, a cutting drum positioned in the external casing and an impeller positioned within the cutting drum.

In yet a further aspect, a method of bone processing includes placing a bone at least partially covered with non-bone tissue comprising at least one of muscle, periosteum and connective tissue inside a sterile casing. The sterile casing includes an impeller and a cutting surface. The impeller is coupled to a power source and the impeller is rotated with the power source to urge the bone against the cutting surface to remove the tissue from the bone.

Another aspect includes a tissue separator having a brushed impeller positioned in a drum. The brushed impeller rotates to remove non-bone tissue from bone.

Another aspect includes a tissue separator having a pressurized fluid nozzle positioned in a drum. Pressurized fluid is directed at bone covered in non-bone tissue to remove non-bone tissue from bone.

DETAILED DESCRIPTION

Figure 1:
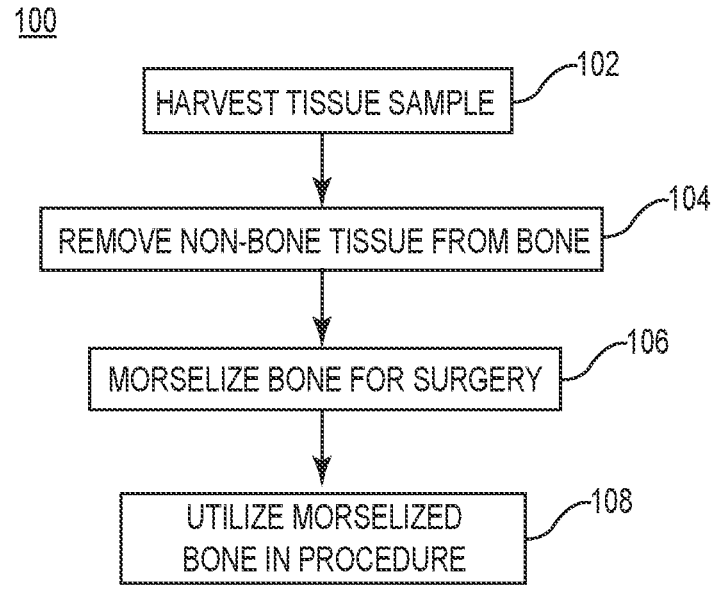
FIG. 1 is a flow diagram of a method of processing bone.
Figure 2:
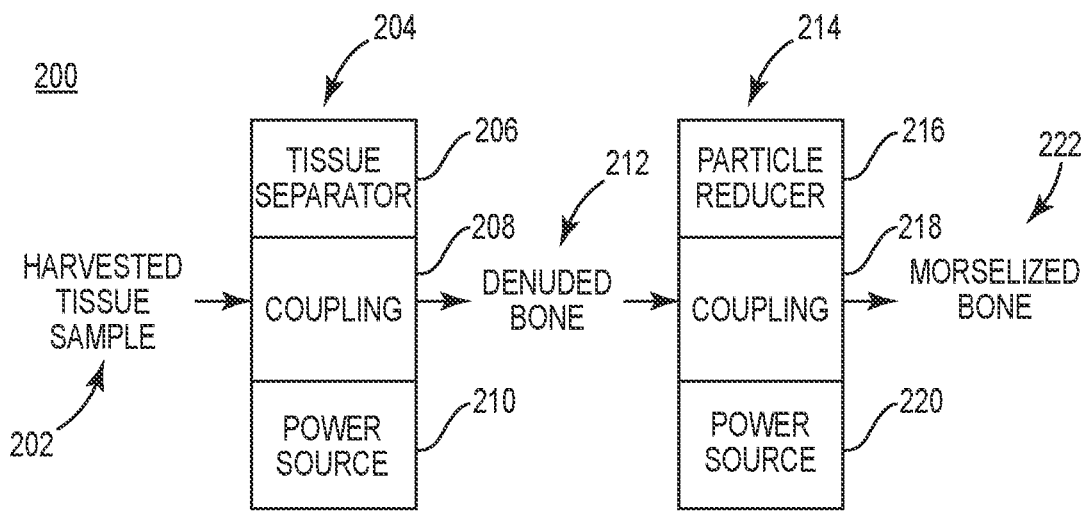
FIG. 2 is a schematic diagram of a bone processing system.

Referring to FIGS. 1 and 2, a method 100 and system 200 are illustrated that can be utilized to process material for medical use. The method and systems below are discussed in terms of autograft from a patient, but is also applicable to other materials such as allograft, synthetic materials, combinations including one or more of autograft, allograft and synthetic materials. Other materials can include bone morphogenic protein (BMP), demineralized bone matrix, hydroxyapatite (HA), coral, etc. In method 100 and system 200, tissue samples 202 are harvested (step 102) from a patient using known surgical bone harvesting techniques. The tissue harvested includes bone and non-bone tissue such as muscle, periosteum and connective tissue. The harvested tissue samples 202 are then placed in a bone denuder 204

(alternatively referred to as a bone denuding device) that removes tissue (step 104) from the bone.

As used herein, denuding relates to removal of non-bone tissue from the bone. In particular, bone denuder 204 includes a tissue separator 206, a coupling 208 and a power source 210. The tissue separator 206 is capable of reducing one or more pieces of harvested tissue 202 into denuded bone 212. As used herein, denuded bone is bone that is substantially free of non-bone tissue such as muscle, periosteum and connective tissue. Power source 210 can take many forms such as an electric motor, pneumatic supply, manual crank, etc. The power source 210 is used for moving the tissue separator 206 in an automatic fashion. The coupling 208 couples the power source 210 to the tissue separator 206, and in some embodiments, may allow for relatively easy connection and disconnection of the particle reducer to and from the power source 210. In one embodiment, tissue separator 206 is removed from the coupling 208 and turned over to empty the denuded bone 212.

The denuded bone 212 is then placed in a bone mill 214, which moreselizes the bone (step 106) for use in surgery. The bone mill 214 also includes a particle reducer 216, a coupling 218 and a power source 220. The particle reducer 216 is capable of reducing one or more pieces of denuded bone into smaller particles to create moreselized bone 222. The power source 220 is used for moving the particle reducer 216 in an automatic fashion and can take various forms such as an electric motor, pneumatic supply, manual crank, etc. Coupling 218 is used for connecting the power source 220 to the particle reducer 216, and in some embodiments, may allow for relatively easy connection and disconnection of the particle reducer 216 to and from the power source 220. Morselized bone particles 222 can then be utilized in a procedure, such as a medical or surgical procedure (step 108). Example procedures include, but are not limited to, spinal fusions (e.g., lumbar, thorasic, cervical), hip implants, orthopedic procedures, autograft procedures, allograft procedures, maxofacial procedures, cranial procedures, tissue banking, research and mastoidectomies.

Although bone denuder 204 and bone mill 214 are illustrated as separate components, it is worth noting that the bone denuder 204 and bone mill 214 can be integrated together and/or share one or more components such as a motor, coupling, external casing, etc. For example, tissue separator 206 of bone denuder 204 and particle reducer 216 of bone mill 214 can each form sterile casings that are selectively coupled to a coupling and power source to perform bone processing steps 104 and 106. In this example, tissue separator 206 and particle reducer 216 can form sterilized casings that are single-use or, alternatively, sterilized after each use. Additionally, although bone denuder 204 and bone mill 214 are illustrated in a generally upright, vertical orientation, the bone denuder 204 and bone mill 214 can be oriented in a generally horizontal orientation or other orientation as desired.

Figure 3:
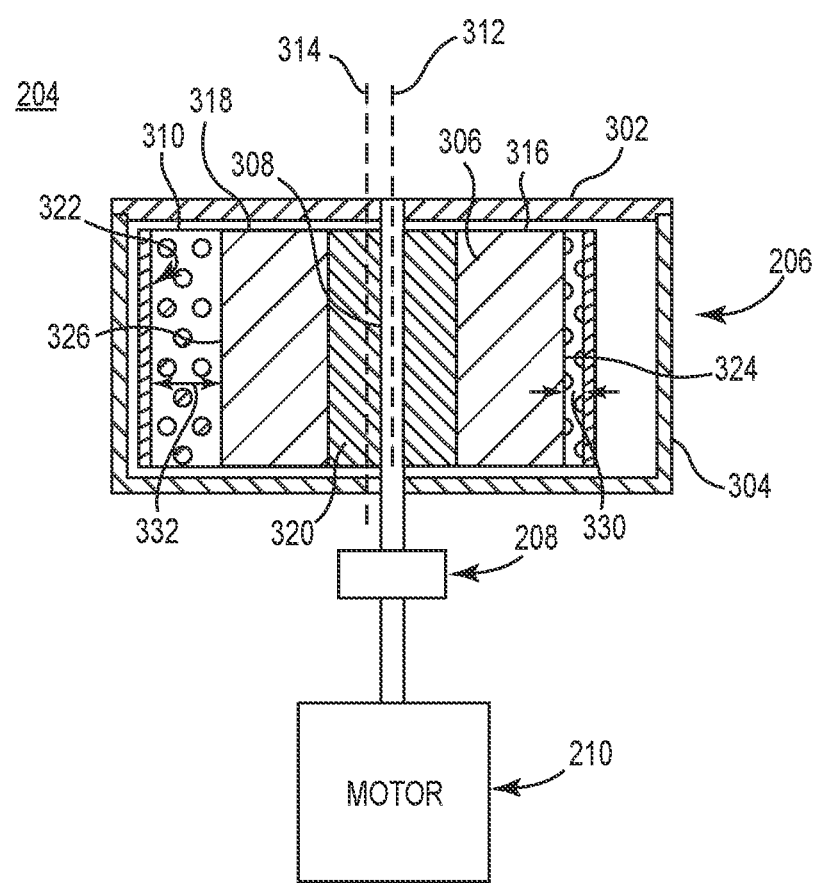
FIG. 3 is a schematic, sectional view of a bone denuder.

FIG. 3 is a schematic, sectional view of bone denuder 204. In the illustrated embodiment, tissue separator 206 includes a cap 302, an exterior casing 304, an impeller 306, a shaft 308, and a cutting drum 310. During use, cap 302 is secured to the casing 304 and impeller 306 is positioned within cutting drum 310. In other embodiments, cap 302 can be excluded. For example, exterior casing 304 can be formed of a split clam-shell design or simply a tubular design with openings for which harvested tissue samples pass through tissue separator 206 from a first open end to a second open end. Shaft 308 is coupled to power source 210 through coupling 208. Impeller 306 is coupled to shaft 308 in order to rotate therewith. As discussed above, impeller 306 and shaft 308 can be oriented in a generally vertical orientation (as illustrated) or in a generally horizontal orientation as desired. As impeller 306 rotates, tissue samples are pushed against cutting drum 310 in order to remove non-bone tissue from the bone. In one embodiment, impeller 306 and shaft 308 are offset with respect to cutting drum 310 such that a central axis 312 shared by impeller 306 and shaft 308 is laterally displaced from a central axis 314 of drum 310. That is to say, impeller 306 and shaft 308 are eccentrically located with regards to cutting drum 310. As a result, there exists a non-uniform positioning between edges of the impeller 306 and cutting drum 310, as explained below.

Impeller 306 includes a first blade 316 and a second blade 318 extending radially from a hub 320 toward an interior cutting surface 322 of cutting drum 310. In alternative embodiments, impeller 306 includes only a single blade. First blade 316 includes a blade edge 324 and a second blade 318 includes a blade edge 326. Illustratively, first blade 316 and second blade 318 are of similar length and blade edges 324 and 326 extend substantially parallel to cutting surface 322. Due to the eccentric relationship between impeller 306 and drum 310, a non-uniform positioning between blade edges 324, 326 and the cutting surface 322 is established. The non-uniform positioning can be described with respect to a first minimum distance 330 from cutting surface 322 to blade edge 324 that is less than a second minimum distance 332 from cutting surface 322 to blade edge 326.

As impeller 306 rotates about shaft 308, the distance between blade edges 324, 326 and cutting surface 322 changes based on the eccentric relationship between impeller 306 and cutting drum 310. Other blade edges of the impeller are positioned at distances between distance 330 and distance 332 depending on the respective radial position of the blade edge. Upon a 180° rotation of impeller 306, blade edge 324 will be positioned at distance 332 from surface 322 whereas blade edge 326 will be positioned at distance 330 from surface 322. In one embodiment, distance 330 is substantially zero such that blade edge 324 is in close proximity to or contacting surface 322. Put another way, blade strain and/or interference between blades of impeller 306 and cutting drum 310 vary with angular displacement of impeller 306.

As an alternative to positioning impeller 306 eccentrically within cutting drum 310, a length of individual blades of impeller 306 can be adjusted so as to create non-uniform positioning between edges of the blades and cutting surface 322. For example, impeller 306 and cutting drum 310 could be positioned concentrically, wherein some blades could be positioned at varying distances from cutting surface 322. The distances can be gradually varied so as to provide similar relative distances between blade edges of impeller 306 and cutting surface 322 as the eccentric relationship depicted in FIG. 3. In any event, these alternative embodiments can vary blade strain and/or interference between blades of impeller 306 and cutting drum 310 with angular displacement of impeller 306.

Figure 4:
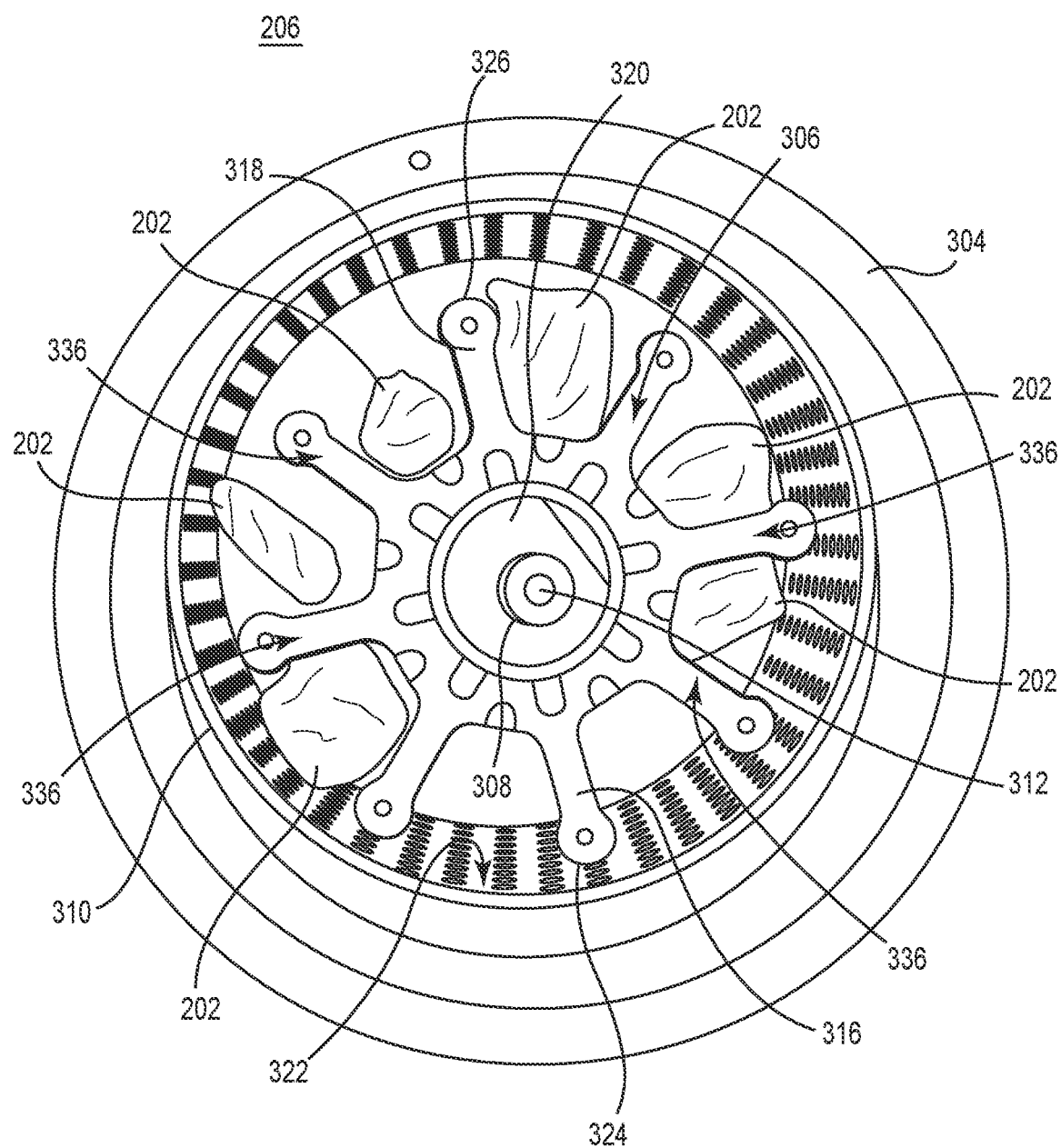
FIG. 4 is a perspective view of a tissue separator of a bone denuder having a first embodiment of an impeller.

With further reference to FIG. 4, impeller 306 includes a plurality of blades 336 extending radially outward from central axis 312. Each of the plurality of blades 336 is of similar length, with respective edges extending substantially parallel to cutting surface 322. Based on the radial position of each blade, a distance from its respective edge to cutting surface 322 (and thus blade strain and/or interference) will vary due to the eccentric relationship between impeller 306 and drum 310. In one example, impeller 306 is formed of a plastic or rubber material exhibiting a durometer approximately in the range of 50 Shore A to 97 Rockwell M and, in a specific embodiment, is around 70 Shore A. In any event, impeller 206 can be formed from a flexible material exhibiting a low flexural modulus, such as a polymer, or through a material exhibiting low section modulus geometry, such as a thin cross section. Alternatively, impeller 306 could be formed of hinged blades.

Moreover, as illustrated, a number of blades in the plurality of blades 336 is eight, although any number of blades can be used, for example any number of blades in a range at of at least one blade to more than ten blades. For example, the number of blades can include at least one blade, at least two blades, at least five blades and at least eight blades. During operation, the plurality of blades 336 cooperates with the cutting surface 322 to cycle harvested tissue 202 through random paths in which the tissue 202 frictionally engages the cutting surface 322 at different positions given the rotational force of impeller 306.

In one embodiment, the cutting surface 322 is formed of a plurality of perforations formed in the cutting drum 310. The perforations include round holes that aid in removing the non-bone tissue and the rotational force of impeller 306 forces non-bone tissue out of drum 310 through the perforations and into the external casing 304. Alternatively, the perforations can be various regular and irregular forms such as rectangles, slits, triangles, etc. In another embodiment, cutting surface 322 need not include perforations and instead can include a plurality of raised or recessed cutting edges that engage bone to remove non-bone tissue therefrom.

Figure 5:
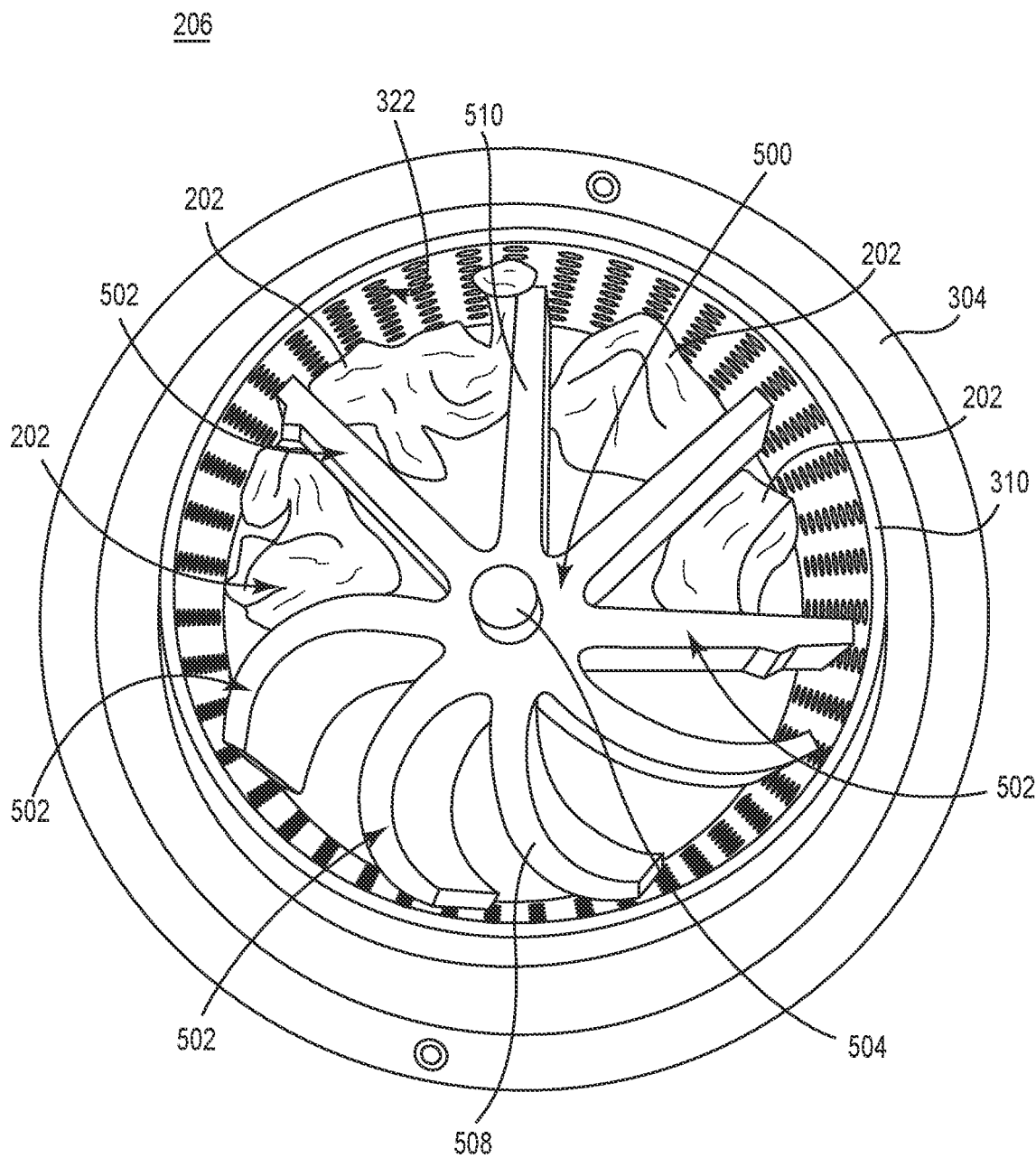
FIG. 5 is a perspective view of a tissue separator of a bone denuder having a second embodiment of an impeller.

In yet another alternative embodiment illustrated in FIG. 5, an alternative impeller 500 is positioned in cutting drum 310. Impeller 500 includes a plurality of blades 502 configured to rotate about a shaft 504. Each of the plurality of blades 502 are of similar length and their respective blade edges extend parallel to cutting surface 322. In contrast to impeller 306 of FIG. 3, the plurality of blades 502 of impeller 500 deflect upon rotation of impeller 500 as the blades come into contact with cutting surface 322. For example, blade 508 is in a deflected (i.e., bent) position, whereas blade 510 extends substantially straight from shaft 504. As impeller 500 rotates 180° with respect to the position in FIG. 5, blade 510 would be in a deflected position whereas blade 508 would extend substantially straight from shaft 504.

Regardless of the particular configuration of the impeller (e.g., 306 or 500), harvested tissue samples are positioned within cutting drum 310 so as to remove non-bone tissue therefrom and produce denuded bone. As the impeller rotates, individual blades of the impeller force the tissue samples against the cutting surface of the cutting drum. The non-uniform relationship between the tips of blades and the cutting surface allows the tissue samples to contact the cutting surface at random positions so as to denude the bone to a sufficient level for use as is or in a bone milling process. In one embodiment, the impeller rotates at a rate greater than 200 revolutions per minute and, in a specific embodiment, at a rate of around 2,000-5,000 revolutions per minute.

Several other configurations for tissue separator 206 can be utilized to denude bone from harvested tissue samples. For example, in one embodiment, a drum (e.g., drum 310) is configured to rotate while an impeller (e.g., impellers 306, 500) remains stationary. In an alternative embodiment, both the drum and impeller rotate, either in the same direction or in opposite directions. If both the impeller and drum rotate, one of the impeller or drum can rotate faster than the other. In other embodiments, the drum and impeller can be coaxial. Further exemplary concepts for tissue separator 206 are illustrated in FIGS. 6-13, described below.

Figure 6:
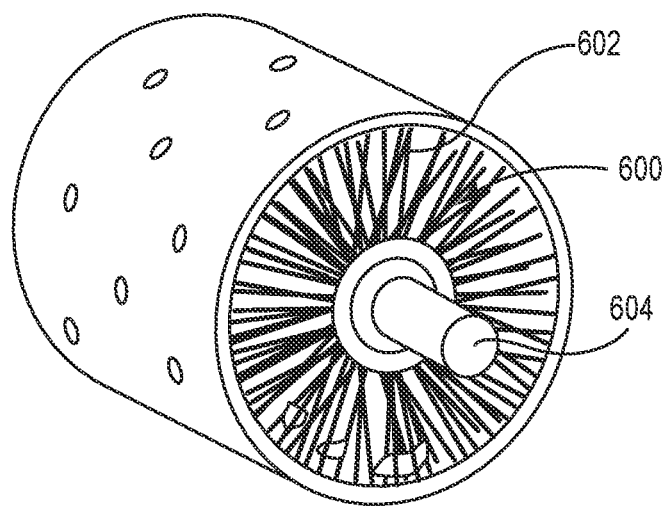
FIG. 6 is a perspective view of a tissue separator of a bone denuder having a third embodiment of an impeller.

FIG. 6 illustrates an alternative embodiment in which a brushed impeller 600 is positioned within drum 310. The brushed impeller 600 includes radially projecting bristles 602 arranged to extend from a central shaft 604 of the impeller 600. Bristles 602 can be formed of various different materials. For example, the bristles may be metal, such as stainless steel, or polymeric, such as nylon. In one embodiment, the bristles 602 can be coated and/or impregnated with an abrasive ceramic, such as silicon carbide and/or alumina. Impeller 600 can be operated up to 100,000 revolutions per minute, and in a particular embodiment, in a range of 700 to 10,000 revolutions per minute to remove non-bone tissue from harvested tissue samples.

Figure 7:
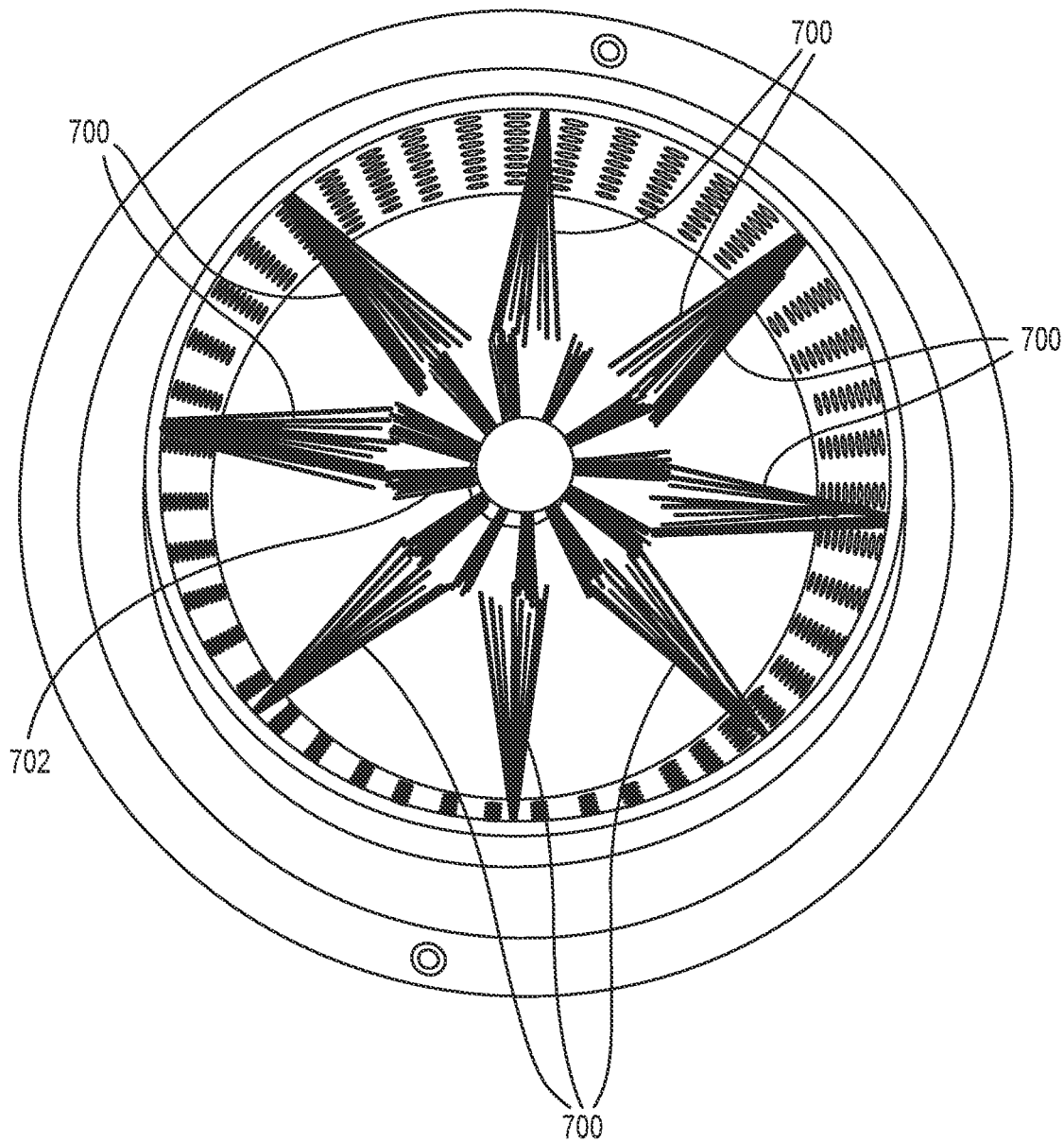
FIG. 7 is a perspective view of a tissue separator of a bone denuder having a drum and a plurality of bristles extending radially inward from the drum.

FIG. 7 illustrates another alternative embodiment, for tissue separator 206, in which bristles 700 can be attached to drum 310 and extend inwardly toward a brushed impeller 702. The radially inwardly extending bristles 700 can act to increase friction between tissue samples as impeller 600 forces tissue samples against the bristles.

Figure 8:
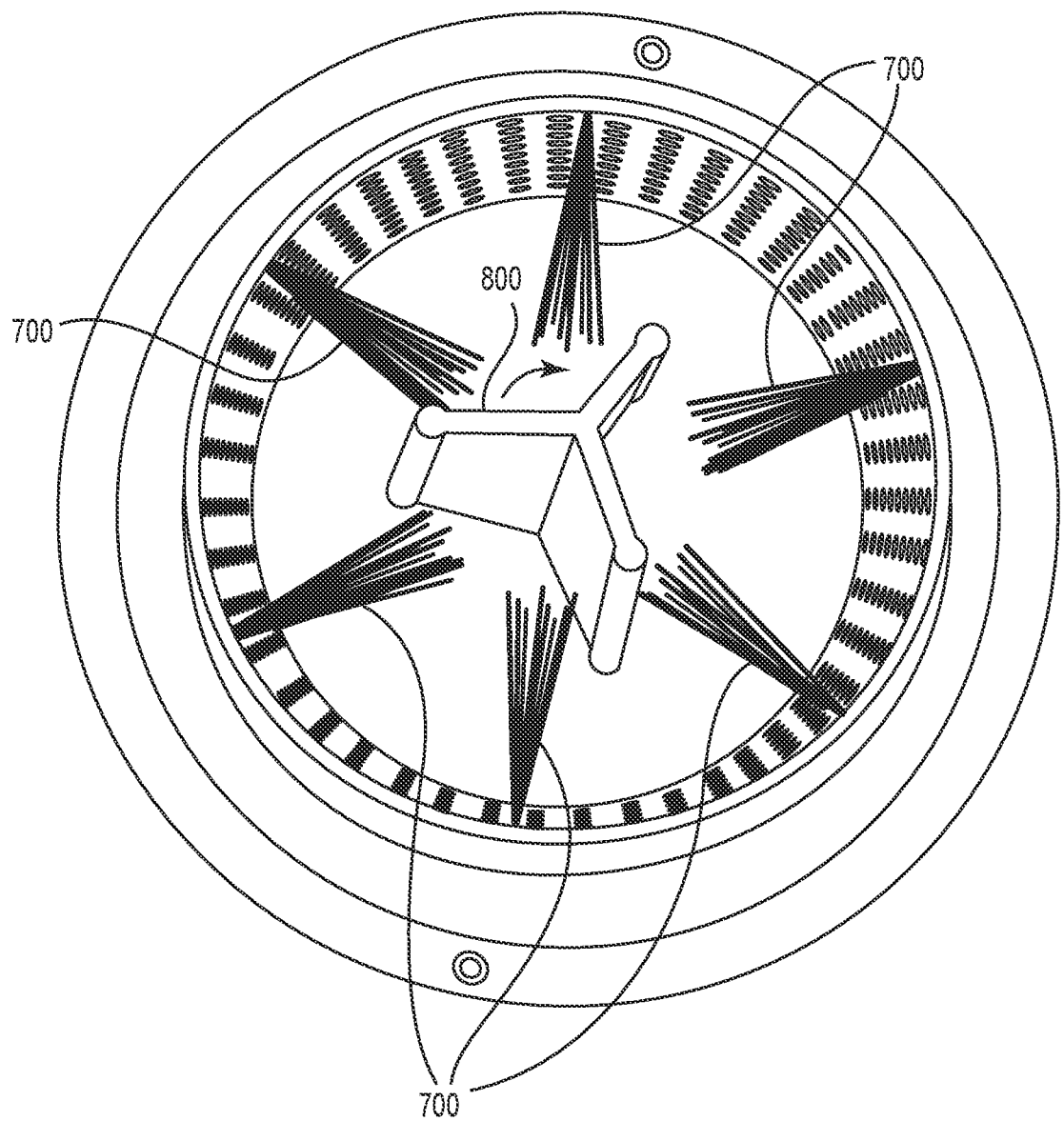
FIG. 8 is a perspective view of the tissue separator of FIG. 7 with an alternative impeller.

In another alternative embodiment, illustrated in FIG. 8, an impeller 800 can replace brushed impeller 600 such that relative motion occurs between impeller 800 and the radially extending bristles 700. Impeller 800, in one embodiment, comprises a polymer material.

Figure 9:
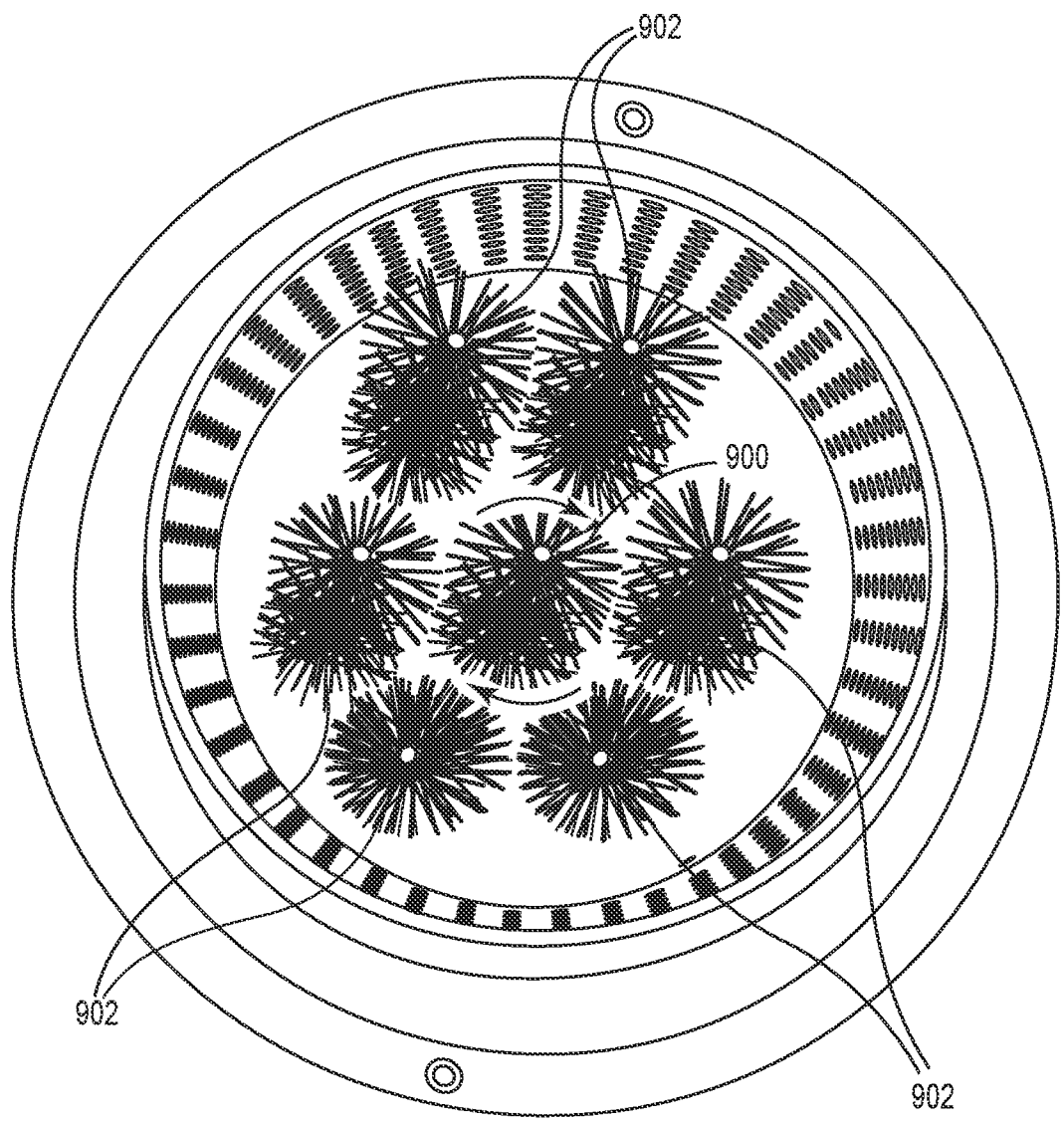
FIG. 9 is a perspective view of a tissue separator of a bone denuder having a plurality of brushed impellers.

In yet another alternative embodiment, a plurality of brushes can be provided within drum 310, as illustrated in FIG. 9. The plurality of brushes includes a central brush 900 and a plurality of radial brushes 902 extending around central brush 900. In one embodiment, radial brushes 902 can be fixed and remain stationary with regard to the central brush 900. Central brush 900 rotates and tissue samples are subject to friction between brushes 900 and 902. In an alternative embodiment, central brush 900 can remain stationary while radial brushes 902 rotate. In yet a further embodiment, all of the brushes 900 and 902 rotate. In any event, in embodiments in which multiple brushes rotate, a single input shaft and a sun/planet gear configuration can be used to transmit rotational force to the brushes.

Figure 10:
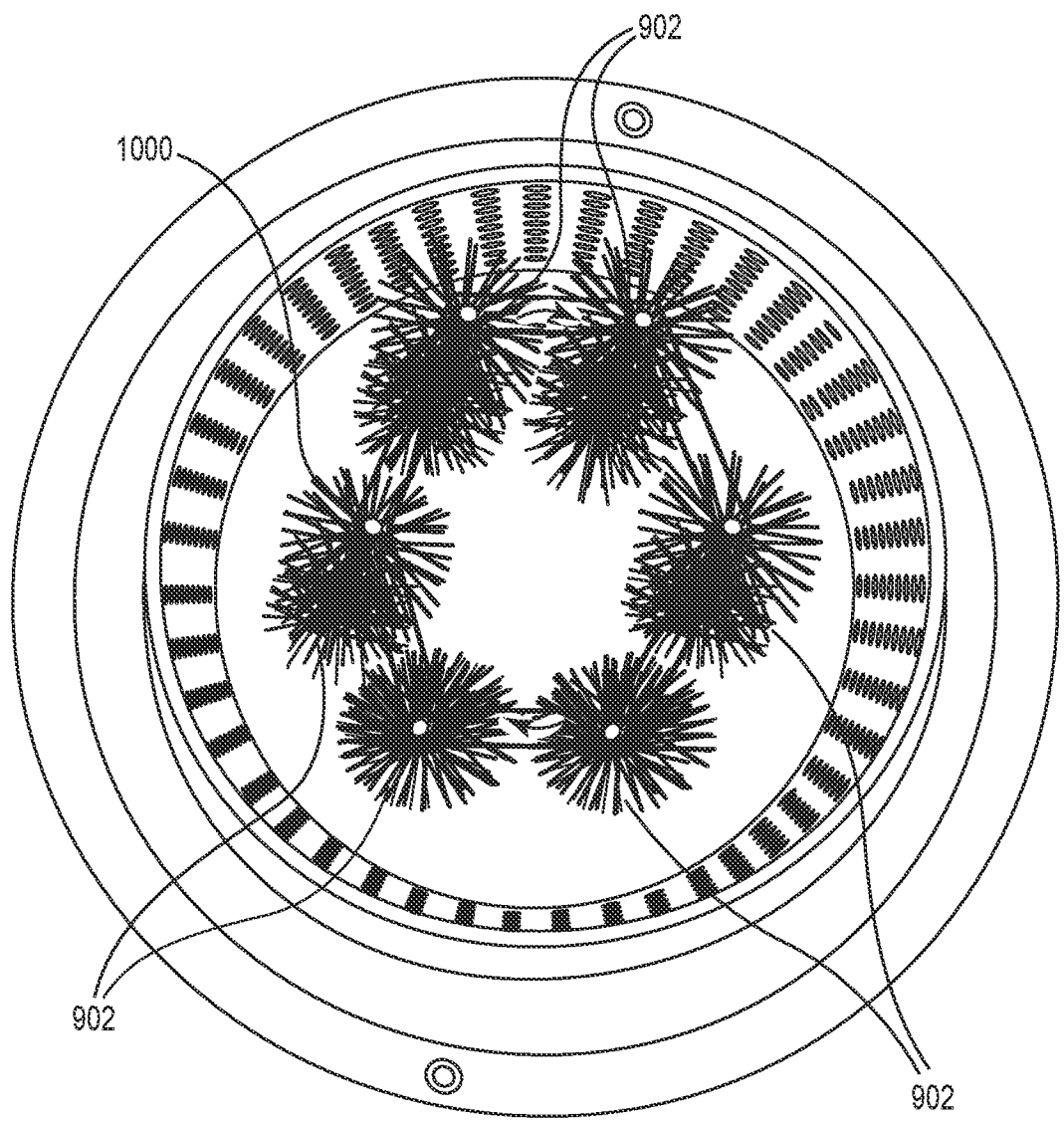
FIG. 10 is a perspective view of a tissue separator of a bone denuder having a plurality of brushed impellers coupled to a carrier.

In another embodiment, as illustrated in FIG. 10, central brush 900 is removed and radial brushes 902 are coupled together on a carrier 1000 that provides translational motion of the brushes 902 relative to the drum 310 while the brushes 902 rotate.

Figure 11A:
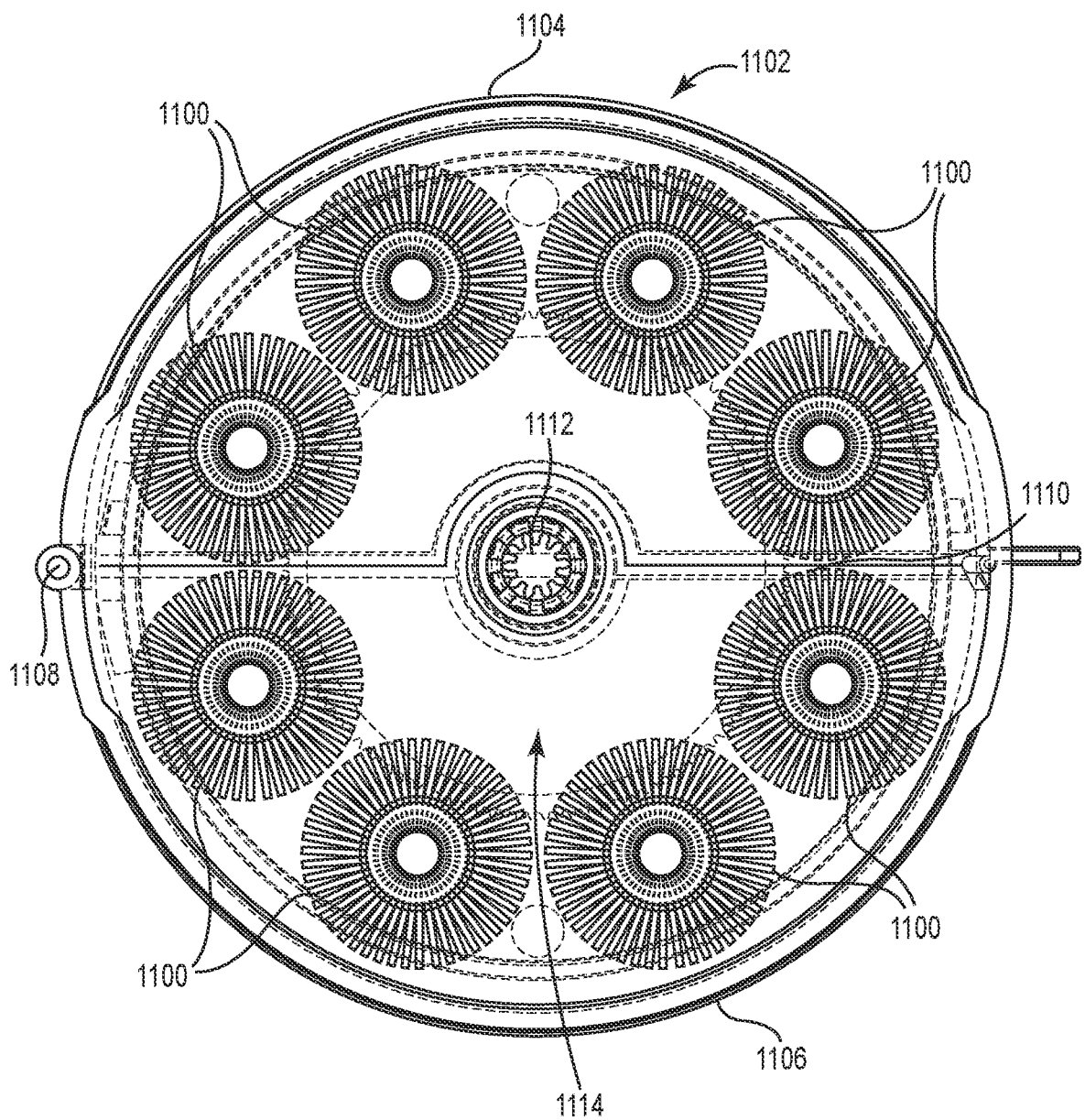
FIG. 11A is a top view of a tissue separator of a bone denuder having a plurality of brushed impellers positioned about a circumference of a drum.
Figure 11B:
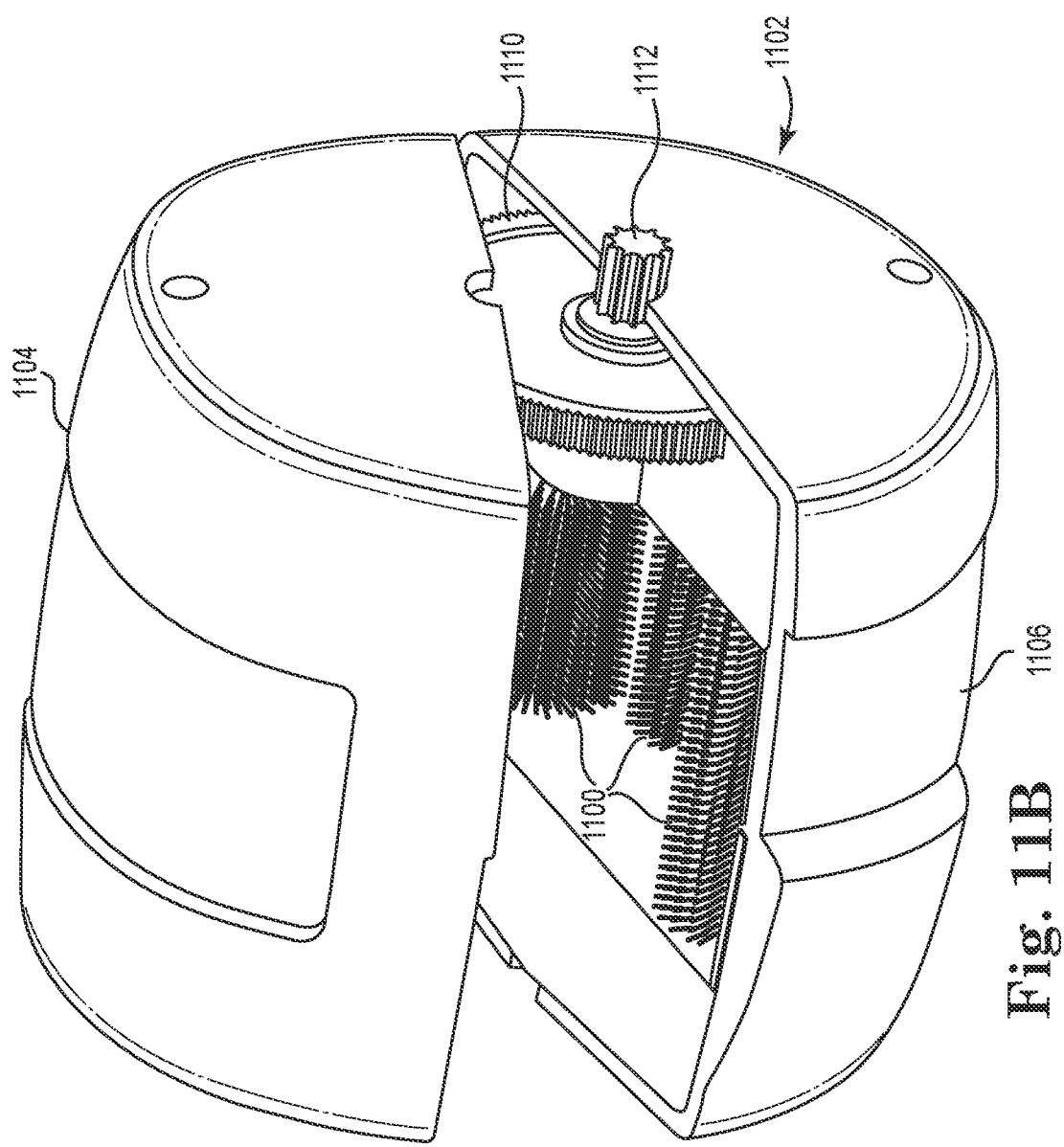
FIG. 11B is a perspective view of the tissue separator of FIG. 11A.

FIGS. 11A and 11B illustrate another embodiment of tissue separator 206, including a plurality of brushes 1100 positioned around a circumference of cylindrical casing 1102. Casing 1102 is formed of two hemispherical halves 1104 and 1106 joined together at a hinge 1108. A gear 1110 is coupled to corresponding gears (not shown) for each of the plurality of brushes 1100 such that rotation of gear 1110 causes rotation of the plurality of brushes. A central shaft 1112 is coupled to a power source in order to provide rotational force to gear 1110. During operation, harvested tissue of bone and non-bone tissue is positioned in a central area 1114 and the plurality of brushes 1100 are caused to rotate. This rotation separates non-bone tissue from bone and transfers the non-bone tissue toward casing 1102 (i.e. away from central area 1114) whereas bone remains in central area 1114.

Figure 12:
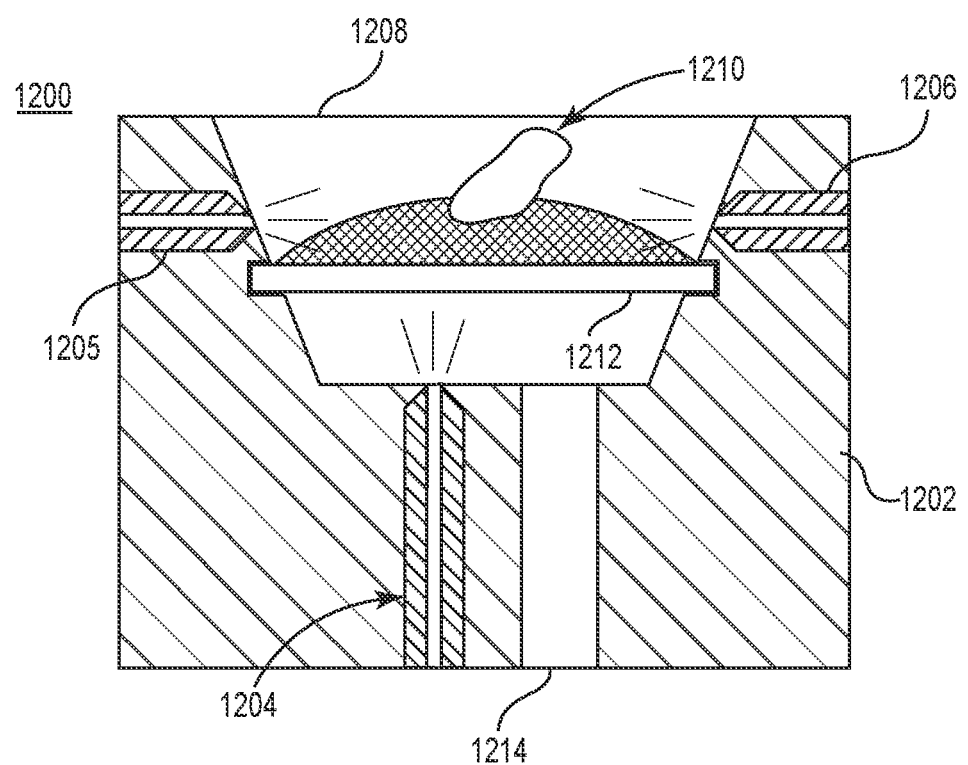
FIG. 12 is a sectional view of a tissue separator of a bone denuder having a plurality of nozzles delivering pressurized fluid.

In still other embodiments, denuding may be accomplished through the use of a pressurized fluid and/or media. Embodiments in FIGS. 12-14 below discuss tissue separation with the use of fluid. However, in other embodiments, the fluid can further include media such as a sterile, biocompatible material such as titanium. In other embodiments, the media can include dry ice, which is utilized to freeze and separate non-bone tissue from bone. As illustrated in FIG. 12, particle reducer 1200 includes a container 1202, nozzles 1204, 1205 and 1206 and a cap 1208. The nozzles 1204-1206 direct and concentrate an energy of fluid and/or media under pressure onto a tissue sample 1210. The pressurized fluid works to separate muscle and connective tissue from bone in the tissue sample 1210. In one embodiment, a screen 1212 is utilized to filter the separated muscle and connected tissue from the bone, which can be drained through an opening 1214 in the container. In one embodiment, the pressurized fluid is sterile water or saline and can be directed at a level of 100 to 100,000 pounds per square inch. In a more particular embodiment, the fluid can be directed at a level of 1,000 to 20,000 pounds per square inch. Nozzles 1204-1206 can be any type of nozzle in which to spray fluid. In one embodiment, the nozzles can be a "turbo" nozzle wherein a narrow jet creates a radially moving pressure spray. Alternatively, the nozzles can be connected to a power source to move the nozzle laterally or in a rotational direction, as desired. In other embodiments, one or more of the nozzles 1204-1206 can be removed. In yet further embodiments, other nozzles can be added, for example adjacent any of the nozzles 1204-1206 and/or coupled to cap 1208.

Figure 13:
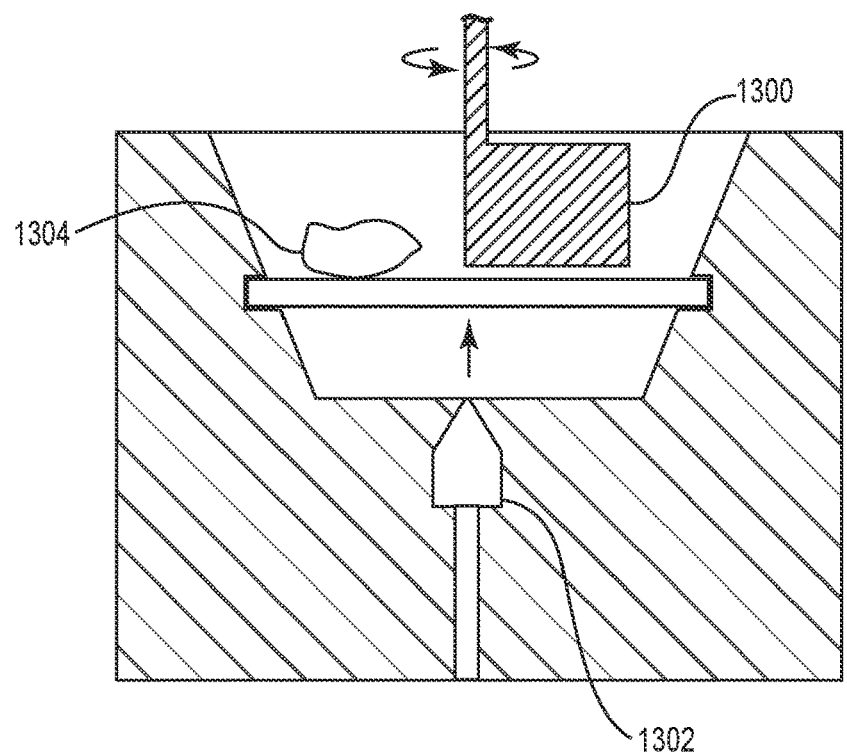
FIG. 13 is a sectional view of a tissue separator of a bone denuder having a nozzle delivering pressurized fluid and a rotating impeller.

FIG. 13 illustrates yet another alternative embodiment, where an impeller 1300 or other rotational member is utilized in combination with a nozzle 1302 in order to move tissue sample 1304 and expose the tissue sample to pressurized fluid from nozzle 1302.

Figure 14:
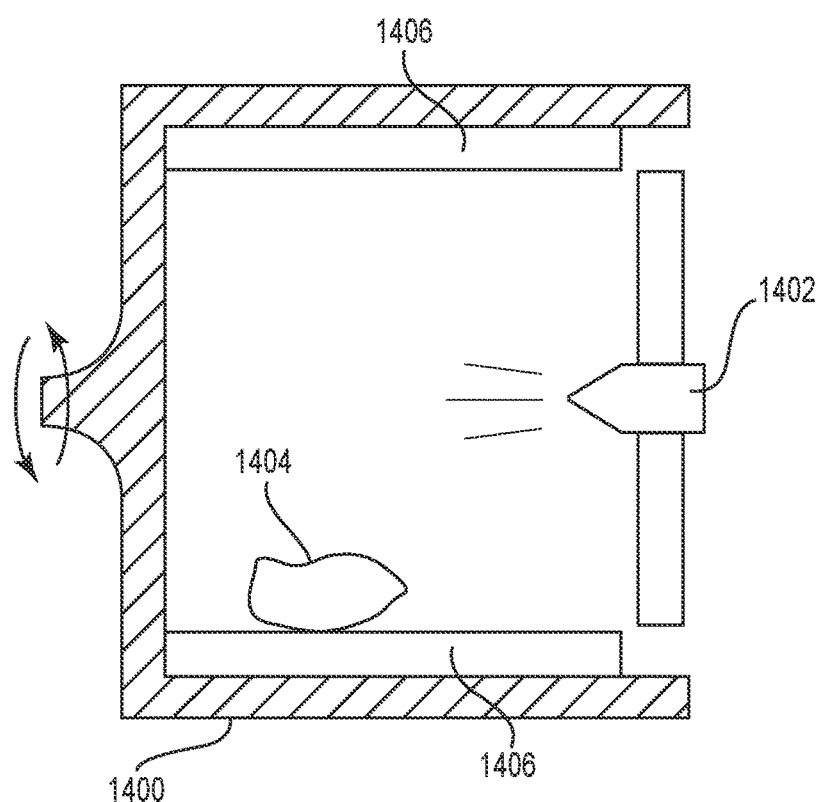
FIG. 14 is a sectional view of a tissue separator of a bone denuder having a rotating drum and a nozzle delivering pressurized fluid.

In the embodiment illustrated in FIG. 14, a rotating drum 1400 is provided wherein a nozzle 1402 directs pressurized fluid toward a tissue sample 1404. If desired, radial projections 1406 can be provided around a circumference of drum 1400 such that sample 1404 tumbles against projections 1406 and into the pressurized fluid stream created by nozzle 1402.

With reference to FIG. 2, once the bone has been denuded by bone denuder 204, the denuded bone can be further processed by bone mill 214 to produce morselized bone particles for use in a procedure. One exemplary bone mill that can be used is described in U.S. Pat. No. 6,824,087, entitled "Automatic Bone Mill", the contents of which are hereby incorporated by reference in their entirety. By utilizing both bone denuder 204 and bone mill 214 in an automatic fashion, an efficient bone processing system is established that can efficiently process bone for medical or surgical procedures in a safe and sterile manner.

Although the concepts presented herein have been described with reference to preferred embodiments, workers skilled in the art will recognize that changes can be made in form and detail without departing from the spirit and scope of the concepts.

What is claimed is:

1. A bone denuder comprising:
    a cutting drum having a cutting surface;
    an impeller positioned within the cutting drum;
    a shaft coupled to the impeller to rotate therewith; and
    a power source coupled to the shaft to provide rotational force thereto,
    wherein the impeller is eccentric with respect to the cutting drum.

2. The bone denuder of claim 1, wherein the cutting drum includes an interior cutting surface.

3. The bone denuder of claim 2, wherein the cutting surface is formed of a plurality of perforations.

4. The bone denuder of claim 2, wherein the cutting surface is formed of at least one raised cutting edge.

5. The bone denuder of claim 1, wherein the impeller includes at least one blade radially extending from the shaft.

6. The bone denuder of claim 5, wherein the impeller includes a plurality of blades and edges of the plurality of blades are positioned with respect to the cutting surface such that blade strain and interference with the cutting surface varies with angular displacement of the impeller.

7. The bone denuder of claim 5, wherein the impeller includes at least three blades.

8. The bone denuder of claim 5, wherein the impeller includes a plurality of blades and edges of the plurality of blades extend substantially parallel to the cutting surface.

9. A bone denuder comprising:
    a cutting drum having a cutting surface, the cutting drum rotatable about a central axis; and
    an impeller positioned within the cutting drum and configured to operably engage a shaft for rotation about a common axis, the shaft adapted to couple to a power source to provide rotational force thereto,
    wherein the common axis shared by the impeller and the shaft is laterally offset from the central axis of the cutting drum.

10. The bone denuder of claim 9, wherein the cutting surface of the cutting drum is an interior cutting surface.

11. The bone denuder of claim 9, wherein the cutting surface includes a plurality of perforations defined therein.

12. The bone denuder of claim 9, wherein the cutting surface includes one or more raised or recessed cutting edges.

13. The bone denuder of claim 9, wherein the impeller includes at least one blade radially extending from the shaft.

14. The bone denuder of claim 9, wherein the impeller includes a plurality of blades, and wherein respective edges of the plurality of blades are positioned with respect to the cutting surface such that blade strain and interference with the cutting surface varies with angular displacement of the impeller.

15. The bone denuder of claim 9, wherein the impeller includes at least three blades.

16. The bone denuder of claim 9, wherein the impeller includes a plurality of blades and wherein respective edges of the plurality of blades extend substantially parallel to the cutting surface.

* * * * *